(12) United States Patent
Kerdiles et al.

(10) Patent No.: US 7,740,735 B2
(45) Date of Patent: Jun. 22, 2010

(54) TOOLS AND METHODS FOR DISUNITING SEMICONDUCTOR WAFERS

(75) Inventors: Sebastien Kerdiles, Saint-Ismier (FR); Yves-Matthieu Le Vaillant, Grenoble (FR)

(73) Assignee: S.O.I.Tec Silicon on Insulator Technologies, Bernin (FR)

( * ) Notice: Subject to any disclaimer, the term of this patent is extended or adjusted under 35 U.S.C. 154(b) by 760 days.

(21) Appl. No.: 11/567,417

(22) Filed: Dec. 6, 2006

(65) Prior Publication Data

US 2007/0093039 A1 Apr. 26, 2007

Related U.S. Application Data

(62) Division of application No. 10/733,470, filed on Dec. 12, 2003, now Pat. No. 7,187,162.

(60) Provisional application No. 60/446,552, filed on Feb. 12, 2003.

(30) Foreign Application Priority Data

Dec. 16, 2002 (FR) .................................. 02 16902

(51) Int. Cl.
*B32B 38/10* (2006.01)
(52) U.S. Cl. ...................... 156/344; 156/584; 29/239; 438/458
(58) Field of Classification Search ................. 156/344, 156/584; 438/455, 458; 29/239
See application file for complete search history.

(56) References Cited

U.S. PATENT DOCUMENTS

| 4,059,470 | A | 11/1977 | Primavesi et al. ........... 156/238 |
|---|---|---|---|
| 5,133,824 | A | 7/1992 | Huberts et al. .............. 156/344 |
| 5,269,873 | A | 12/1993 | Platzer et al. ............... 156/584 |
| 5,374,564 | A | 12/1994 | Bruel ........................... 437/24 |
| 5,447,596 | A | 9/1995 | Hayase ........................ 156/584 |
| 5,989,386 | A * | 11/1999 | Elliott ......................... 156/344 |
| 6,215,643 | B1 | 4/2001 | Nagasaki ..................... 361/234 |
| 6,351,367 | B1 | 2/2002 | Mogi et al. .................. 361/234 |
| 6,436,226 | B1 | 8/2002 | Omi et al. .................... 156/344 |
| 6,468,879 | B1 | 10/2002 | Lamure et al. .............. 438/458 |
| 6,521,078 | B2 | 2/2003 | Yanagita et al. ............. 156/344 |
| 6,746,559 | B2 | 6/2004 | Ohmi et al. ................. 156/239 |
| 2002/0036373 | A1* | 3/2002 | Kosakai ........................ 269/21 |
| 2003/0089455 | A1* | 5/2003 | Sakaguchi et al. .......... 156/344 |

(Continued)

FOREIGN PATENT DOCUMENTS

EP 0 432 832 A1 6/1991

(Continued)

*Primary Examiner*—Mark A Osele
(74) *Attorney, Agent, or Firm*—Winston & Strawn LLP

(57) ABSTRACT

A tool and method for disuniting two wafers, wherein at least one of the wafers is used in fabricating substrates for microelectronics, optoelectronics, or optics. The method includes the steps of temporarily affixing two gripper members to respective opposite faces of the wafers; and sufficiently displacing one of the gripper members relative to the other for inducing controlled flexing in at least one of the members and for exerting a force close to one edge of the wafers to assist in disuniting the wafers. If desired, the bonding energy between two wafers can be determined by measuring the force exerted during the displacement step or measuring the separation of the wafers while performing the disuniting operation.

8 Claims, 10 Drawing Sheets

U.S. PATENT DOCUMENTS

2005/0150597 A1    7/2005    Henley et al.  ............... 156/344

FOREIGN PATENT DOCUMENTS

| | | |
|---|---|---|
| EP | 0 989 593 A2 | 3/2000 |
| FR | 2 572 216 A1 | 4/1986 |
| GB | 2 124 547 A | 2/1984 |
| JP | 60-196644 A | 10/1985 |
| WO | WO 00/26000 A1 | 4/2000 |

* cited by examiner

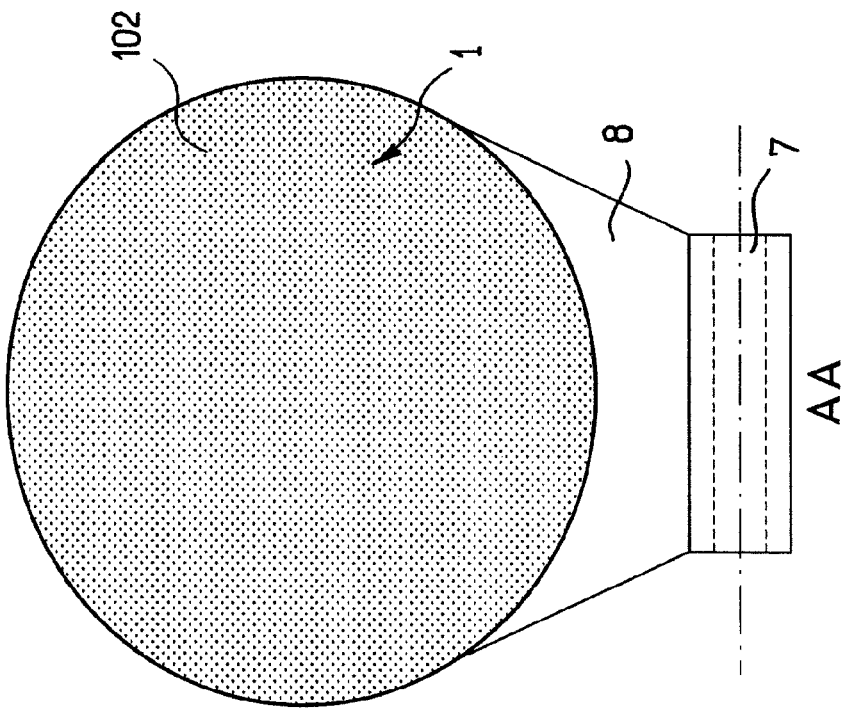
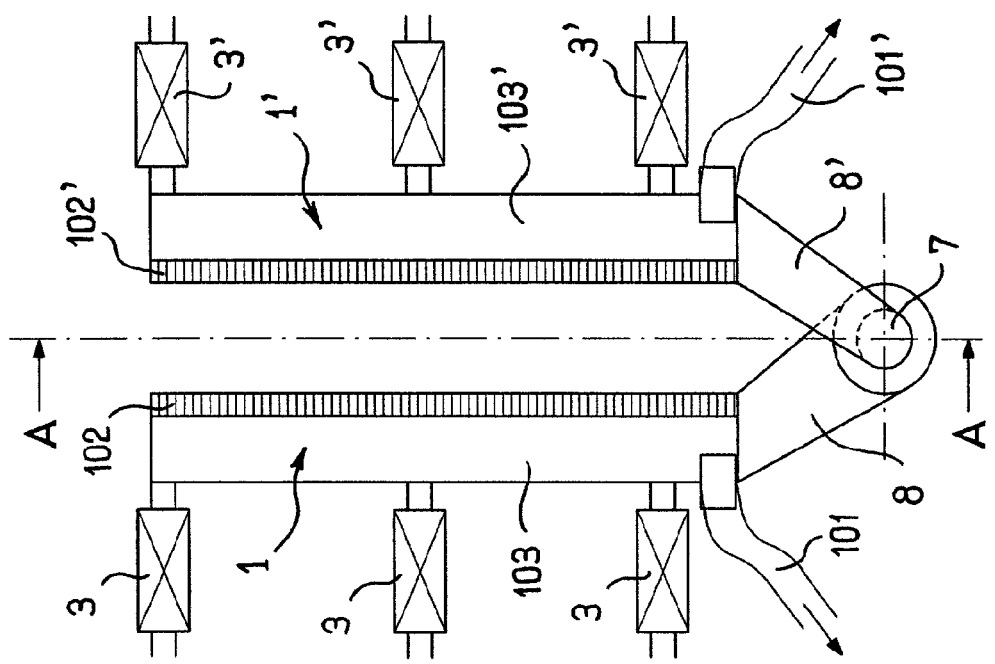
FIG.3A
FIG.3B

AA

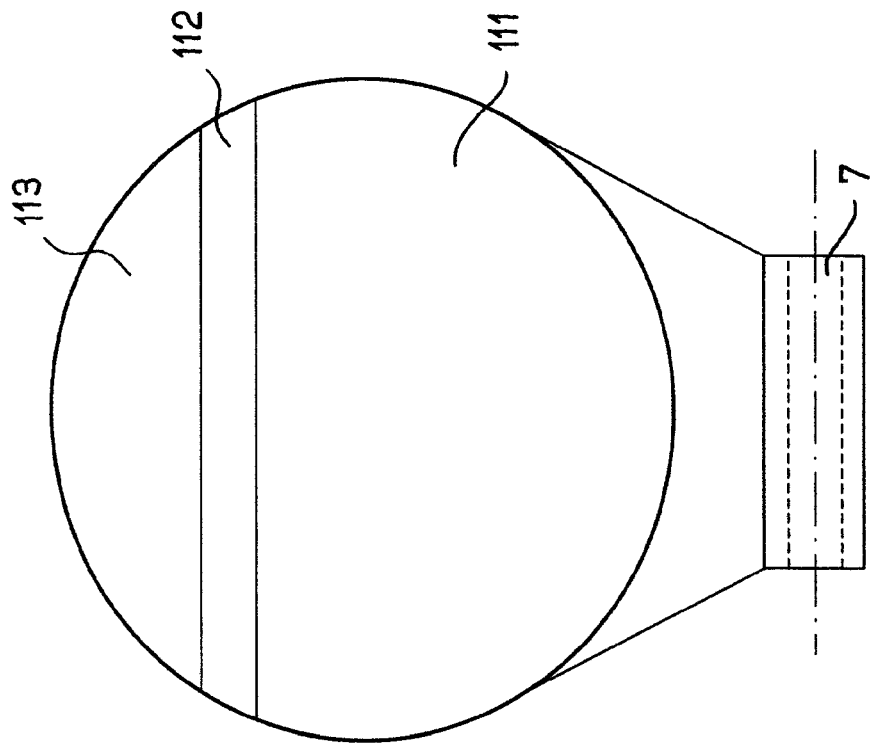
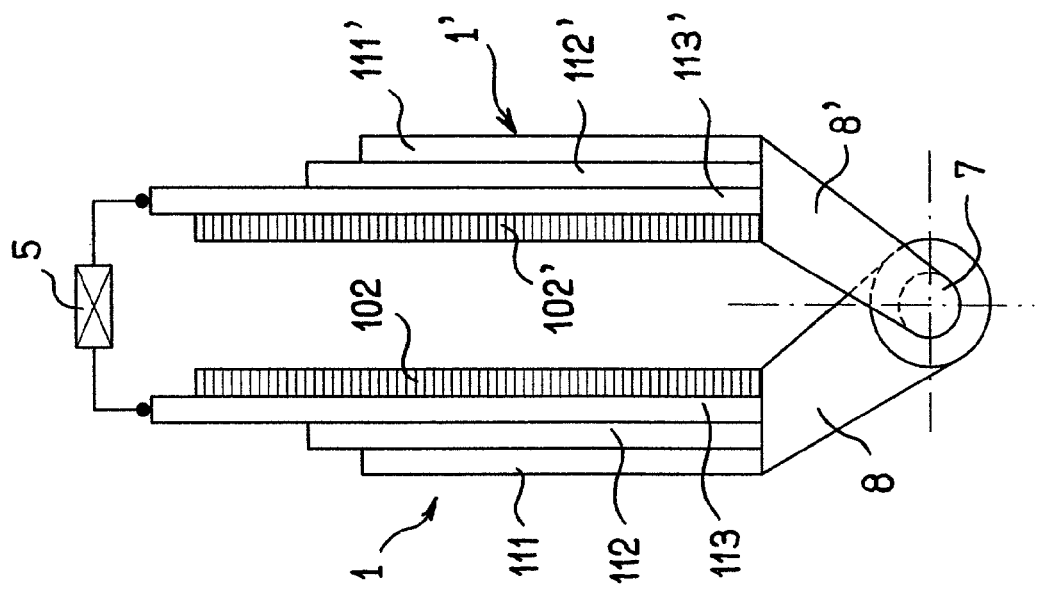
FIG.5A
FIG.5B

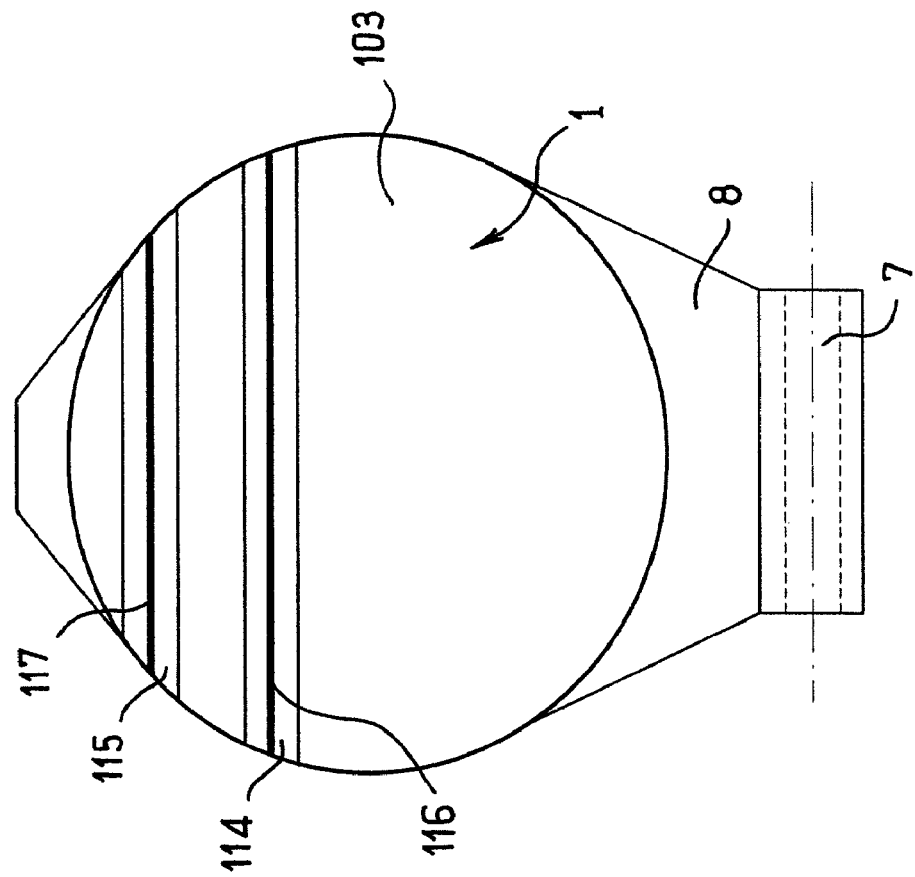
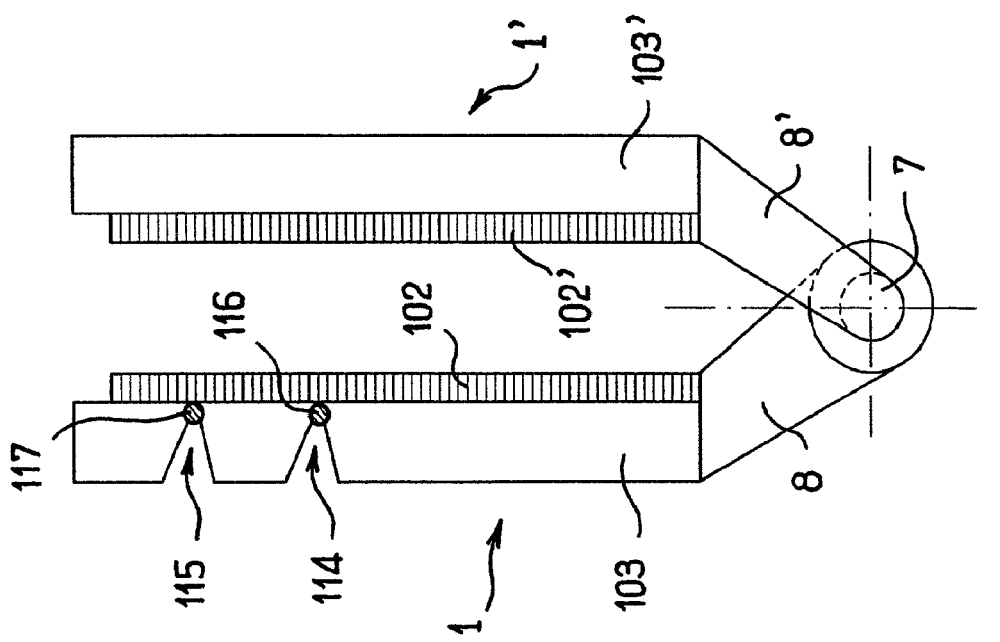
FIG.7B
FIG.7A

TOOLS AND METHODS FOR DISUNITING SEMICONDUCTOR WAFERS

CROSS-REFERENCE TO RELATED APPLICATIONS

This application is a divisional of application Ser. No. 10/733,470 filed Dec. 12, 2003, now U.S. Pat. No. 7,187,162 which application claims the benefit of U.S. provisional application 60/446,552 filed Feb. 12, 2003. The entire content of each prior application is expressly incorporated herein by reference thereto.

BACKGROUND

The present invention relates in general manner to disuniting thin layers in the context of fabricating semiconductor substrates for the microelectronic, optoelectronic, and optic components and related uses.

The present invention also relates to a novel tool for separating a structure in controlled and measured manner at the plane of an interface, in particular at an interface that has been weakened by implanting species using a known method such as the SMART-CUT® method disclosed for example in U.S. Pat. No. 5,374,564.

It is initially recalled that that method implements fracturing at an interface or weakened zone that is obtained by implanting species, typically ions of hydrogen and/or rare gases into a semiconductor material structure or wafer that has been attached by molecular bonding to another wafer that acts as a support. Thus, the SMART-CUT® method makes it possible to provide thin films and to assemble them together in stacked structures from which they can be removed.

The steps of that method are summarized below. Initially, an intermediate bonding layer (typically silica, silicon nitride, palladium, etc.) is generally formed by deposition (or by thermal oxidation for silica on) at least one of the wafers that are to be assembled together. Ions are then implanted using a beam of ions at a single energy over the entire surface of the wafer that is to be made thinner. The implanted ions weaken the material at an interface whose depth is a function of the implantation energy and is typically of the order of 1 micrometer ($\mu$m).

The surfaces of the wafers to be assembled together are subjected to treatment (mechanical and chemical lapping, chemical treatment, etc.) prior to bonding. The implanted plate is then attached to a stiffening substrate by molecular bonding. The bonding force can be increased by annealing for consolidation purposes. Thereafter, the implanted film is fractured at the weakened zone. This fracturing can be achieved in various ways, generally by applying thermal or mechanical energy or both. The final step consists in lapping the surface of the thinned-down film by polishing or lapping either chemically or both chemically and mechanically.

Thus, one of the essential steps of that method is fracturing in the plane of the weakened zone, which step generally relies on the principle of supplying thermal and/or mechanical energy. With thermal fracturing, the implanted species migrate in the plane of the implanted zone and form cavities of gas (a phenomenon referred to as "ripening"). Bonded to a stiffening substrate, the implanted film has its cavities grow preferentially in the plane of the interface where the density of the implanted species is greatest. The last stage of ripening corresponds to the cavities coalescing. Their diameter can then be as great as several micrometers. Forming these cavities serves to further weaken the interface. Forming gas inside the cavities generates pressure that encourages fracturing.

Fracturing by heat treatment is advantageous for industrial implementation because it requires minimal physical handling, however it cannot be achieved with all combinations of materials. Thus, heterostructures possessing layers of materials having very different thermal expansion coefficients (TECs) (e.g. silicon on quartz or sapphire on silicon) cannot be subjected to the heat treatment needed for fracturing without causing irremediable damage to the structure (warping or rupturing). By way of example, a structure comprising silicon on quartz having respective thermal expansion coefficients of $2.6 \times 10^{-6}$ centimeters per degree kelvin (cm/K) and $0.5 \times 10^{-6}$ cm/K breaks prior to reaching the threshold temperature. Fracturing must therefore be finished off mechanically.

In addition, the techniques used in fabricating substrates of the silicon on insulator (SOI) structures require ever finer control over bonding energies.

Bonding can rely on a variety of techniques: molecular bonding (directly or via transition layers); metal bonding; fusion bonding; etc. Bonding energy per unit area depends on numerous parameters: the selected material; the planeness or smoothness of wafer surfaces; roughness; bonding temperature; heat budget of the consolidation treatment; etc.

Studies in this field are therefore very precious in developing products. They make it possible to determine the influence of numerous parameters. However, at present, there are no tools or techniques available on an industrial scale that enable reliable and reproducible measurements of bonding energy to be obtained.

In this regard, and with reference to FIG. 1 of the drawing figures, the preferred prior art technique for commercial use includes inserting a blade 10 at the desired interface between two wafers 11 and 12, and then disbanding the structure in part over a distance that is measured, thus making it possible ultimately to determine the bonding energy.

Still in the context of disuniting wafers, it can be necessary during the technological steps of creating a component to remove a substrate used at the beginning of the method. By way of example, materials having a large forbidden band (based on gallium nitride or other metal nitrides) can be grown epitaxially in industry on a sapphire substrate. After epitaxy, the insulation quality of the substrate prevents any electrical contact being made with the rear face. Thus, when it is desired to use such epitaxy to make a component of vertical geometry (for example a light-emitting diode (LED), or a laser source having a vertical cavity), it can be useful or even essential to remove the substrate. Various technologies have been developed for this purpose: selective chemical etching; mechanical or ion thinning; and the so-called "laser lift-off" technique. This technique consists in disuniting a heteroepitaxial layer from its substrate by using a laser to scan the interface between the substrate and the epitaxially-grown layer.

However all the techniques that have been developed for removing a support that is no longer desired or needed present certain limitations. The technique of chemically etching the substrate destroys it, thus wasting material. Also, the laser life-off technique can generally be performed only over small areas, and not over the entire surface of a substrate having a diameter of about ten centimeters or more.

In order to mitigate these limitations, techniques have begun to be developed involving a "dismountable" substrate. In general, a dismountable substrate presents a multilayer structure: a substrate for epitaxial growth which is of small thickness (typically a few nanometers), providing a lattice parameter that is adapted to epitaxial growth is bonded to a mechanical support that is thick (typically a few hundreds of micrometers). After epitaxy, the idea is to dissociate the two layers of the resulting pseudosubstrate. That technology requires precise control over bonding energy as a function of temperature. More precisely, the bonding energy must be strong enough to accept the temperature required for epitaxial growth and weak enough subsequently to allow the layers to be disunited.

It is then possible to dissociate the pseudosubstrate by applying stress of a different kind, for example mechanical stress. The various techniques presently in existence for disuniting layers are summarized below.

Firstly, as mentioned above, thermal fracturing is typically used in the fabrication of SOI materials. It is obtained by high temperature annealing (typically at a temperature greater than 400° C.). That technique presents several advantages: it is easy to implement industrially, it is repeatable, and the surfaces after fracture are uniform. In addition, high speed annealing furnaces enable high rates of throughput to be achieved.

For mechanical fracturing, there presently exist various ways of proceeding with mechanical disjunction of thin layers. U.S. Pat. No. 6,468,879 describes a tool and a technique in which the structure is disbanded in the weakened interface plane by applying localized deformation action. It uses arms that hold onto opposite sides of the structure by suction, and a trigger system that initiates disbanding by moving the edges of the wafer apart. This localized effect then propagates as a disbanding front to produce disbanding over the entire interface.

A limitation of that approach lies in that it is suitable only for structures having low disbanding energy such as SOI structures made using the SMART-CUT® method, where the energy required for disbanding is greatly reduced by prior heat treatment. For higher disbanding energies, the deformation of the wafers becomes large and can go so far as to damage them. In addition, certain semiconductor materials such as InP present a lower plastic deformation threshold and cannot be used with that kind of technique.

In addition, because of the manual action of the disbanding force, that system does not provide any measurement of the previously-existing bonding energy.

Secondly, British patent application GB-A-2,124,547 discloses a method of cleaving plates that are laminated parallel to their surfaces and describes a tool having grippers that can exert separation stress by applying suction to the plates that are to be cleaved. The grippers can move in parallel or they can pivot about a common axis. Provision is made for the grippers to be ring-shaped.

Nevertheless, the technique described in that document has a metallurgical application and does not appear to be suitable for fragile materials such as semiconductors. In addition, the roughness of the surfaces obtained after such cleaving made in accordance with the teaching of that document appears to be incompatible with present specifications that apply in the field of semiconductors (using magnitudes of angstrom order). Finally, that document does not make provision for measuring bonding energy, nor for measuring the imposed spacing.

Thirdly, a cutting technique using a jet of liquid under pressure is used in a so-called "Eltran" method which consists in growing a film of silicon epitaxially, in bonding it to a mechanical support of silicon oxide, and then in separating the epitaxial film by cutting using a jet of water which can be assisted by other techniques such as inserting blades.

Fourthly, and returning to FIG. 1, when it comes to measuring bonding energy (or surface energy), the technique in which two bonded-together wafers 11 and 12 of respective thicknesses $t_{w1}$ and $t_{w2}$ and with respective Young's moduli $E_1$ and $E_2$ are separated in part by means of a separator such as a razor blade 10 makes it possible by measuring the disbanding length L to calculate the bonding energy using a mathematical formula. In practice, a blade is selected that is of thickness which depends on the stiffness and the size of the bonded substrates. The blade is inserted into the junction, thereby causing partial disbanding. Once this disbanding has stabilized, the disbanded length is measured. The equations enable the bonding energy to be calculated.

However, whether for disbanding implemented in a method of fabrication or used for measuring bonding energy, recourse to blades presents certain limits. Firstly, it is always desirable to initiate disbanding in the weakest region of the implanted interface, and it is difficult to position the blade precisely so as to initiate fracturing at exactly this position. The use of a blade also incurs the risk of scratching the facing surfaces while they are being separated. In addition, when the radius of curvature of the wafers that are being separated becomes too great, such deformation of the wafers can give rise to structural defects such as dislocations. Finally, the principle of that technique does not enable the disbanding energy implemented to be measured in a manner that is sufficiently precise and reproducible, even though attempts have been made in the prior art described above to achieve this with the help of a mathematical model.

Throughout the specification below, the term "disuniting" is used generally. This term thus covers the notion of disbanding structures that have been assembled together (bonding by means of adhesive, of molecular bonding, optionally assisted by surface treatment such as plasmas, of metal bonding, of fusion bonding, etc.). However the term "disuniting" is also used to designate fracturing of the type involving cleaving in a plane parallel to the interface, with a particular example being given by SMART-CUT® method fracturing at the weakened interface, or indeed lift-off at the interface between a substrate and a layer that has been deposited, epitaxially or otherwise.

SUMMARY OF THE INVENTION

In a first aspect, the present invention provides a tool for disuniting two wafers, with at least one of the wafers being used in fabricating substrates for microelectronics, optoelectronics, or optics. The tool comprises two gripper members for temporarily affixing to respective opposite faces of the wafers that are united to each other, and a disuniting control device suitable for moving the members relative to each other. The disuniting control device comprises an actuator device for positively displacing the gripper members sufficiently for inducing controlled flexing in at least one of the members to assist in disuniting the wafers.

In one embodiment, at least one gripper member comprises a diaphragm having a plurality of orifices communicating on one side with a wafer face and on the other side with a vacuum source. Advantageously, each gripper member includes this structure. Preferably, the orifices are micropores.

In another embodiment, at least one gripper member comprises an electrode which has a different potential compared to that of a respective wafer face so as to provide temporary affixing by electrostatic forces. Advantageously, each gripper member includes this structure. Also, each gripper member that includes an electrode preferably comprises dielectric material which surrounds the electrode.

The actuator device can include at least two actuators for acting on at least one gripper member at at least two distinct locations. The particular number of actuators depends upon the size of the united wafer structure and the preciseness of the disuniting.

In a preferred arrangement, at least one gripper member comprises a body generally in the form of a plate having different degrees of elastic deformability in at least two locations. This body may be formed by assembling at least two laminations of different dimensions. Also, the body may be formed by a plate of non-uniform thickness, such as one having a thickness that varies progressively.

In another preferred arrangement, at least one groove is formed locally in the plate. This groove can extend entirely across the plate. Two or more grooves can be used, if desired, with a parallel arrangement being preferred. At least one gripper member can include a member for limiting flexing, preferably one that is adjustable. In this situation, the at least one gripper member in which flexing can be induced includes a member for limiting flexing provided adjacent the groove. For example, the member for limiting flexing may comprise a micrometer screw operating between regions of the plate that are situated on either side of the groove.

In yet another arrangement, the two gripper members are mounted to pivot relative to each other, and the actuator device acts at a distance from the pivot region.

A device for adjusting the spacing between the gripper members can be included so as to enable united wafers of different total thicknesses to be disunited. The actuator device preferably comprises one or more hydraulic actuators. If desired, a device for measuring forces exerted by at least one of the actuators or spacing between the wafers.

Another aspect of the invention relates to an assembly for disuniting a plurality of pairs of united wafers in series, the assembly comprising a plurality of tools as described herein, and a common actuator device engager for jointly displacing at least one gripper member of each tool.

Yet another aspect of the invention relates to a method of disuniting two wafers. This method comprises temporarily affixing two gripper members to respective opposite faces of the wafers; and sufficiently displacing one of the gripper members relative to the other for inducing controlled flexing in at least one of the members to assist in disuniting the wafers.

In this method, the temporary affixing step may comprise contacting the gripper members with the wafer faces by applying a vacuum. Alternatively, the temporary affixing step may comprise providing the gripper members with the wafer faces by applying electrostatic forces. In yet another arrangement, the two gripper members are mounted to pivot relative to each other, and the displacement step comprises mutually displacing regions of the gripper members that are situated at a distance from the pivot region.

The displacement step preferably comprises independently displacing two distinct regions of a single gripper member.

A further aspect of the invention relates to a method of measuring the bonding energy between two wafers. This method comprises temporarily affixing two gripper members to opposite faces of the wafers; displacing one of the gripper members relative to the other sufficiently for inducing controlled flexing in at least one of the aid members in order to disunite the wafers one from the other; and measuring the force exerted during the displacement step or measuring the separation of the wafers while performing the disuniting operation. Preferably, both the force exerted during the displacement step and the separation of the wafers is measured while performing the disuniting operation.

BRIEF DESCRIPTION OF THE DRAWING FIGURES

Other aspects, objects, and advantages of the present invention appear better on reading the following detailed description of preferred embodiments thereof, given by way of non-limiting example and made with reference to the accompanying drawings, in which, FIG. 1 illustrates a preferred prior art technique for commercial use in disuniting wafers;

FIGS. 3A and 3B are respectively a cross-section view and a side elevation view of a tool in a first practical embodiment of the invention;

FIGS. 5A and 5B are views analogous to FIGS. 3A and 3B showing another practical embodiment of the tool;

FIGS. 7A and 7B are views analogous to FIGS. 3A and 3B showing yet another practical embodiment of the tool;

DETAILED DESCRIPTION OF THE PREFERRED EMBODIMENTS

The present invention seeks to mitigate the limitations of the prior art and to propose a disuniting technique which offers at least one of the following advantages:

- the ability to disunite interfaces having high bonding forces, for example of the order of 1 joule per square meter ($J/m^2$) or more;
- the ability to measure bonding energy in a manner that is reasonably precise and reproducible;
- a reduced risk of the disunited wafers being damaged or rupturing; and
- applicability to numerous types of interfaces between wafers such as weakened zones, and various types of controlled bonding, etc.

Figure 1:
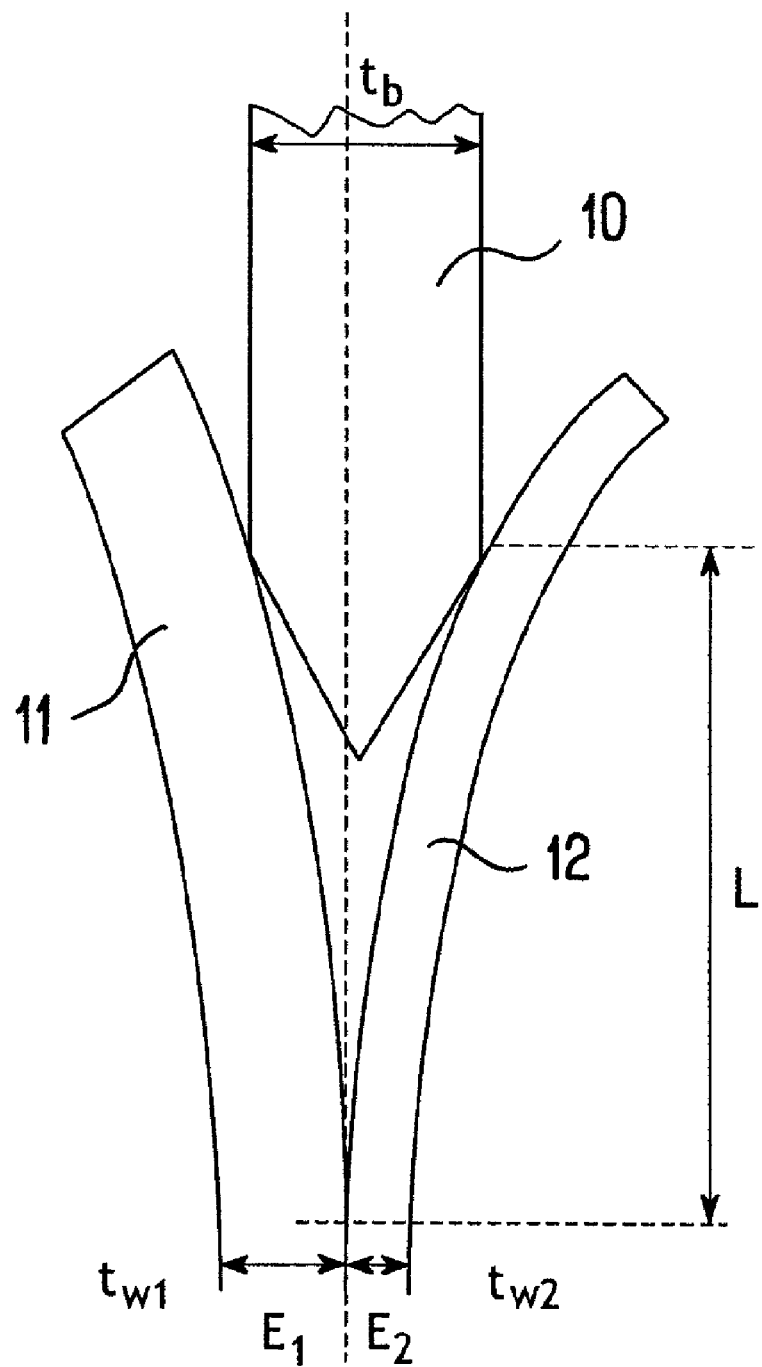
Figure 2:
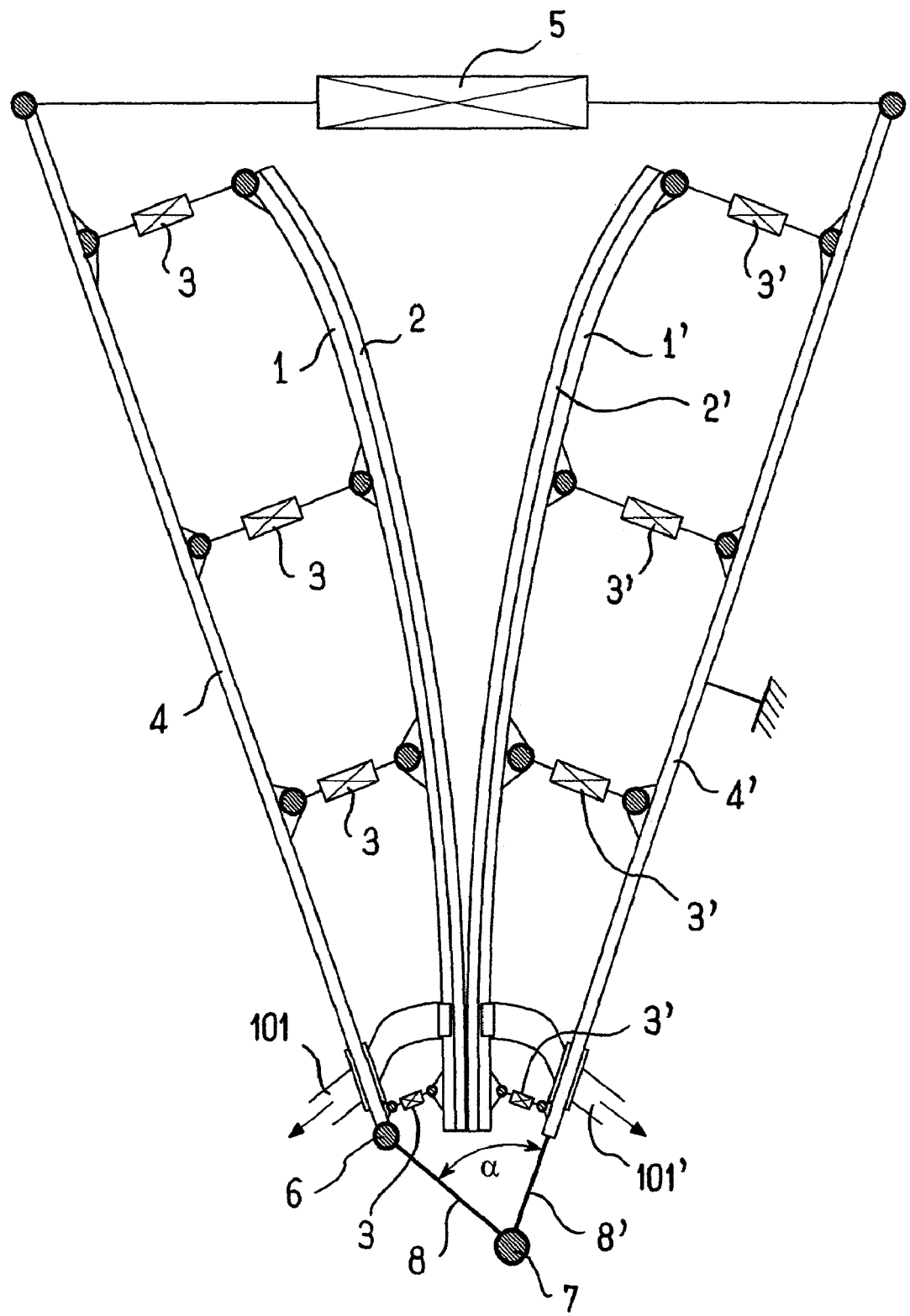
FIG. 2 is a diagrammatic cross-section view of a disuniting tool of the present invention.

With reference now to FIG. 2, there can be seen a disuniting tool made up of two plates 1 and 1' which are both deformable and capable of pivoting one relative to the other under drive from a main actuator 5. These plates are sandwiched on the two faces of the structure that is to be disunited, itself made up of two wafers 2 and 2'. Adhesion is then obtained by vacuum suction. For this purpose and as described in detail below, the plates 1 and 1' are constituted by vacuum chambers and by diaphragms, e.g., ceramic diaphragms, pierced by orifices or micropores enabling suction to be exerted. These plates 1 and 1' are curved by the action of a series of actuators respectively referenced 3 and 3' mounted between the rear faces of the plates 1 and 1' and the facing faces of two rigid slabs 4 and 4'. These slabs are mounted with a single degree of freedom to pivot relative to each other about a pivot axis 6, the slab 4' being stationary by being mounted on a structure. A secondary axis 7 allows means (not shown) to adjust the angle α so as to enable the tool to be adapted to assemblies of wafers 2, 2' of different thicknesses.

By combining pivoting about the axis 6 under the control of the actuator 5 with the deformability of the plates 1 and 1' and with the individualized action of the actuators 3 and 3' which are capable of controlling the deformation of said plates, this tool makes it possible to control the disuniting force in a manner that is localized, precise, and reproducible.

FIGS. 3A and 3B show details of the diaphragm plates 1 and 1' and of the vacuum chamber in a first embodiment. Thus, each plate 1, 1' comprises a main body 103, 103' housing over its entire extent a vacuum chamber (not shown specifically) communicating with a respective duct 101, 101' via which a vacuum source can be applied. In register with each vacuum chamber there extends a respective diaphragm or wall 102, 102' that is porous or pierced by a certain number of orifices, preferably of uniform distribution. The walls 102, 102' can be rigid, or preferably they are flexible.

In this embodiment, pivoting is provided not via the rigid slabs 4, 4' but directly via the deformable plates 1, 1' which possess respective arms 8, 8' hinged about a pivot axis 7. The actuators 3, 3' thus act directly between the slabs 4, 4' and the plates 1, 1' in order both to deform them and to make them pivot. In FIG. 3B, it can be seen that the plates are generally circular in shape, having a diameter which is preferably slightly greater than the diameter of the wafers to be disunited.

Figure 4:
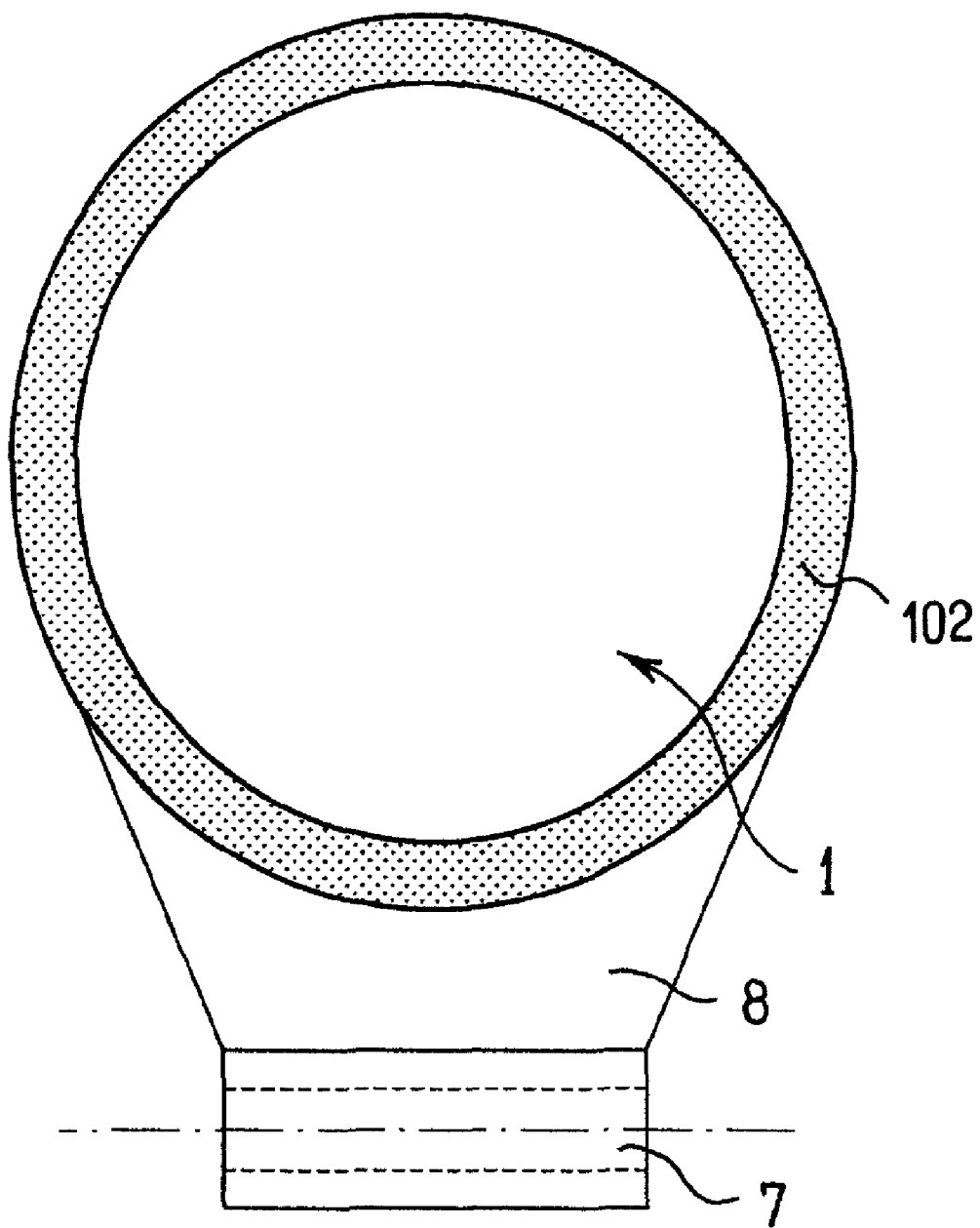
FIG. 4 is a view analogous to FIG. 3B showing an alternate embodiment of a portion of the tool.

FIG. 4 is a view analogous to FIG. 3B and shows an alternative embodiment for the deformable plates 1, 1'. In this case, the plate 1 is provided with its porous or perforated wall 102 solely in a peripheral annular region. The corresponding vacuum chamber extends in register with this annular region. The other plate 1' is preferably of identical design. Such a variant serves to protect the main surfaces of the wafers since the gripper plates 1 and 1' co-operate with them by suction only in a peripheral region.

Although each plate 1, 1' in the embodiment shown in FIGS. 3A and 3B possesses the same intrinsic deformability over its entire extent, and the multiple actuators 3, 3' enable differing amounts of curvature to be given to different regions of the plates 1, 1', it is also possible in another embodiment to act on the curvature of the plates 1, 1' by ensuring that their intrinsic deformability varies between different regions.

Thus, FIGS. 5A and 5B show an embodiment in which each plate 1, 1' is of thickness that varies as a function of the distance from the pivot axis 7, such that the regions furthest from said axis are thinner and more deformable.

In this embodiment, this is obtained by building up the body of each plate by assembling respective laminations 111, 112 & 113 and 111', 112' & 113', these laminations extending over differing areas starting from a common base region beside the pivot axis 7. Specifically, the regions of the plates 1, 1' that are furthest from the axis 7 and adjacent to the region where the force of the main actuator 5 is exerted thus present greater deformability and, under the action of said actuator, bending in these regions is greater than elsewhere.

Figure 6:
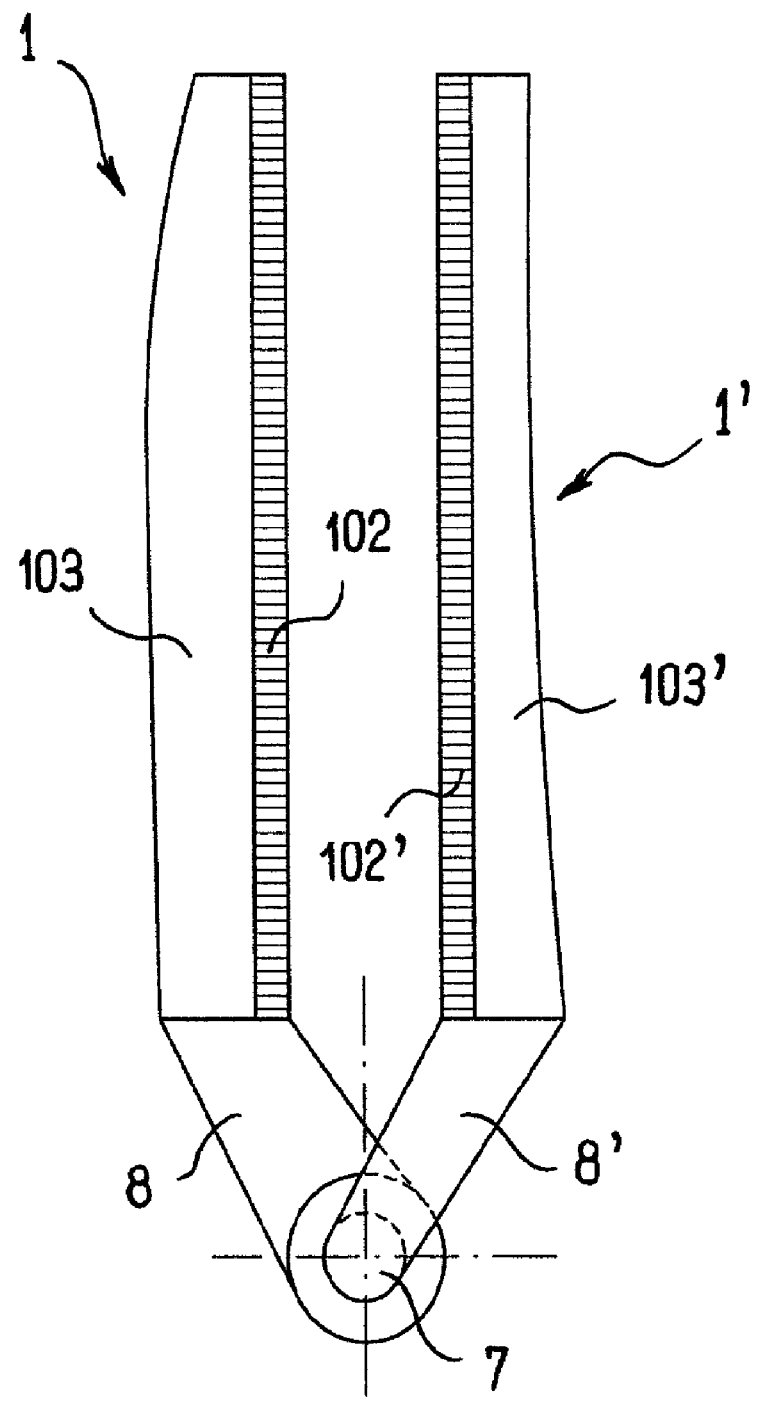
FIG. 6 is a view analogous to FIGS. 3B and 5B showing yet another embodiment of the tool.

Another way of causing the deformability of the plates 1 and 1' to vary consists in making their respective main bodies 103, 103' as single pieces, but of varying thickness, as shown in FIG. 6. In this particular example, the plate 1 is more deformable at its end remote from the region of the pivot 7, while the other plate 1' presents maximum deformability at a distance which is set back a little from said opposite end.

Other embodiments are naturally possible: in particular it is possible to provide laminations made out of materials that differ from one another, and/or laminations that are themselves of varying thickness.

It is also possible to provide for the plate bodies 103, 103' to present constant thickness over their entire extent, but for them to be made out of materials of properties that differ over their extent.

Another possibility is shown in FIGS. 7A and 7B of the drawings. It consists in forming one or more grooves in at least one of the plates (in particular in the plate 1), said grooves being of greater or smaller depth for the purpose of increasing the deformability of the plate in localized manner. Specifically, the main body 103 of the plate 1 shown here possesses two grooves 114 and 115 of depth that is slightly less than the thickness of the body so as to create linear zones 116 and 117 in which flexing is privileged. Such an arrangement can be provided on a single plate or on both plates. In which case, the arrangement of grooves can be identical on both plates or different.

Figure 8:
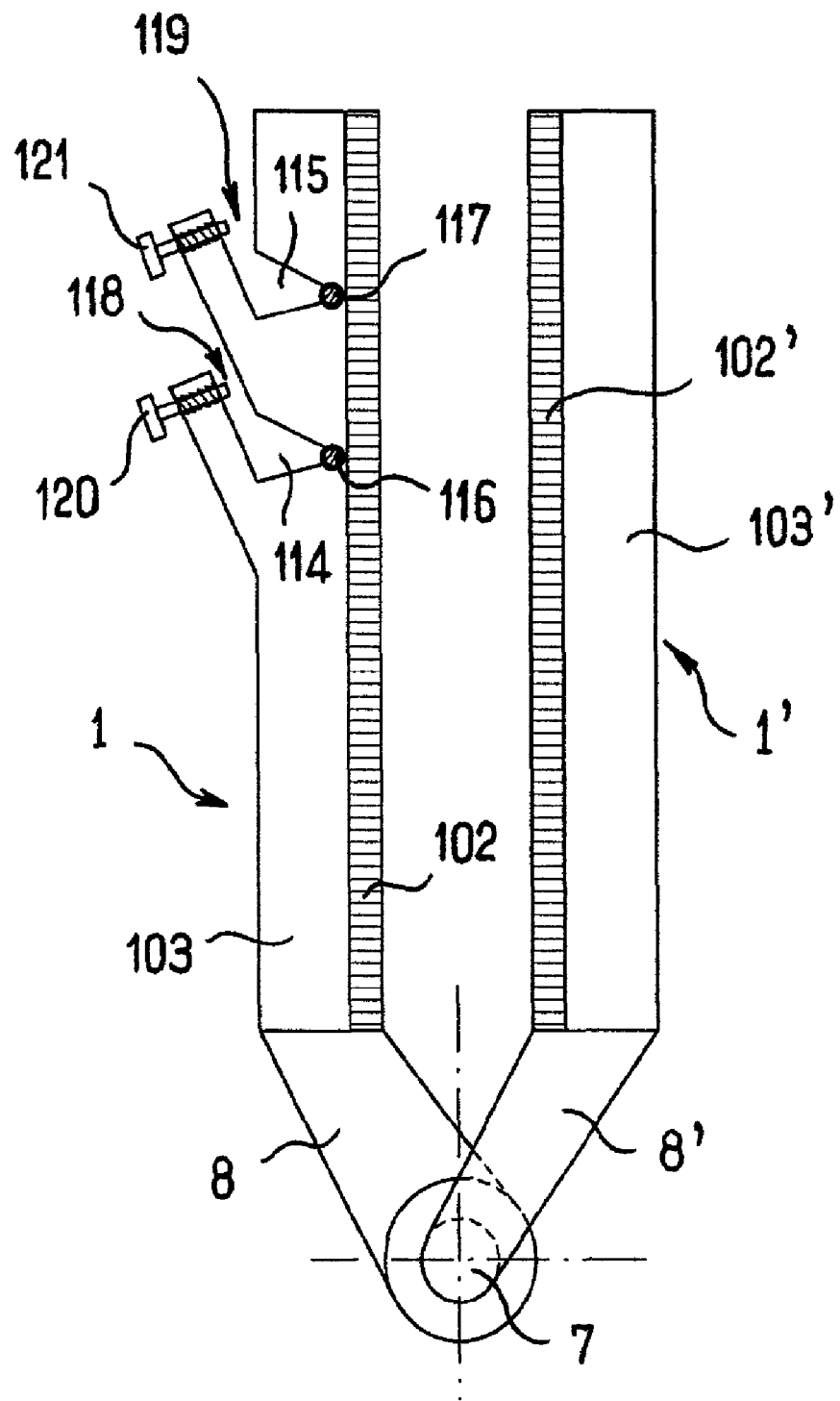
FIG. 8 is a view analogous to FIG. 7A showing a variation of that embodiment.

FIG. 8 shows a variant of the embodiment of FIGS. 7A and 7B in which flexing in the privileged zones 116 and 117 can be limited by means of abutment members. In this example, these abutment members are in the form of two micrometer screws 120 and 121 mounted in flanges adjacent to the grooves 114 and 115 and they serve to limit the widths of respective channels 118 and 119 defined between portions of the main body (including said flanges) extending on either side of the respective grooves.

In yet another variant, it is possible to provide gripper diaphragms 102, 102' of different diameters, and more generally of different dimensions, for use in disuniting structures that are asymmetrical. For example the structure may comprise one substrate having a diameter of 50 millimeters (mm) placed on another substrate having a diameter of 100 mm.

Figure 9:
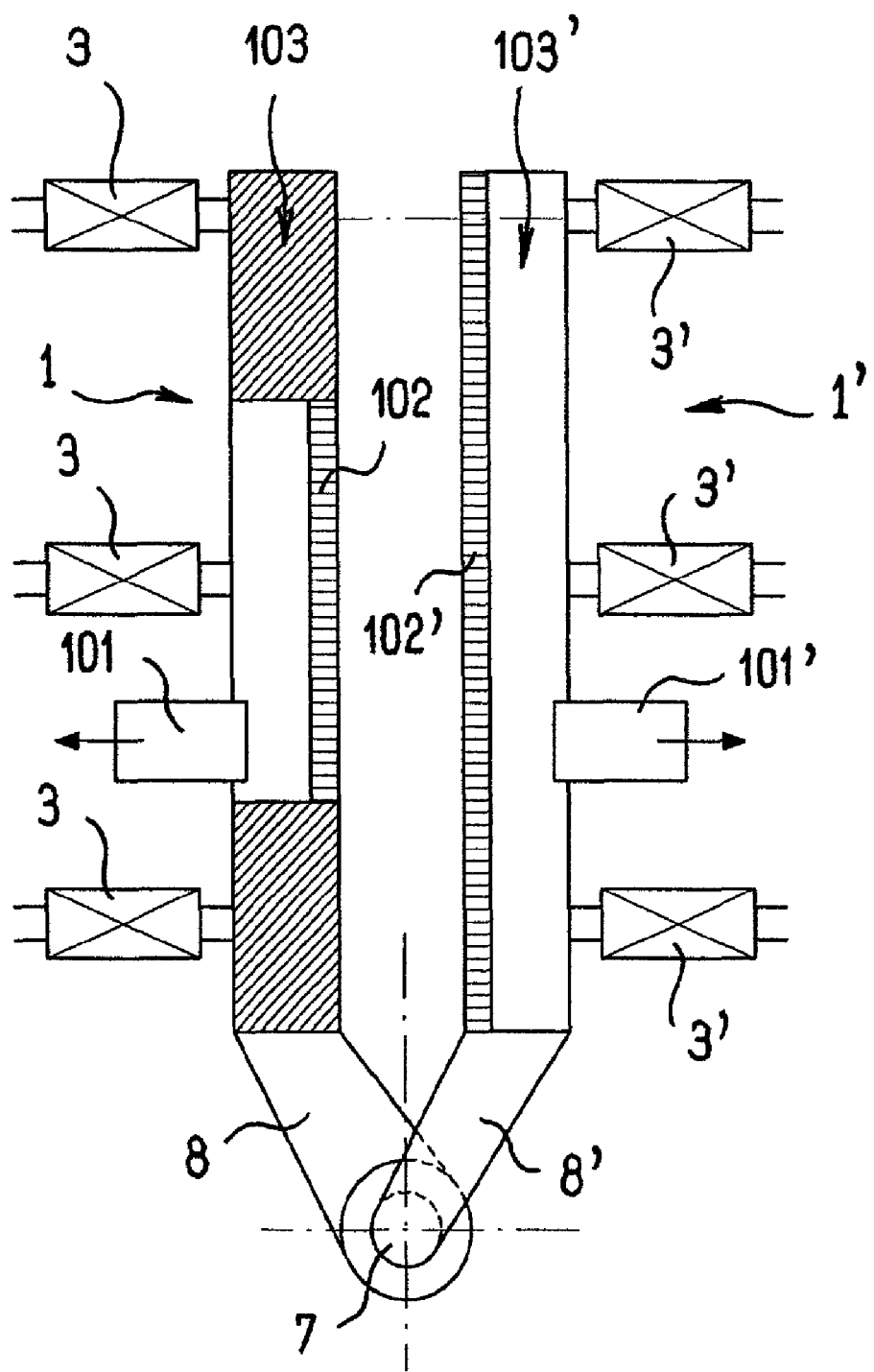
FIG. 9 is a view analogous to FIGS. 3A, 5A, and 7A, showing an embodiment adapted to separating wafers of different dimensions.

Thus, and as shown in FIG. 9, the plate 1 possesses a gripper diaphragm 102 that is smaller than the diaphragm 102' fitted to the plate 1'. The corresponding vacuum chambers which are of extents represented by the shaded zones in FIG. 9, are preferably adjusted accordingly.

Figure 10:
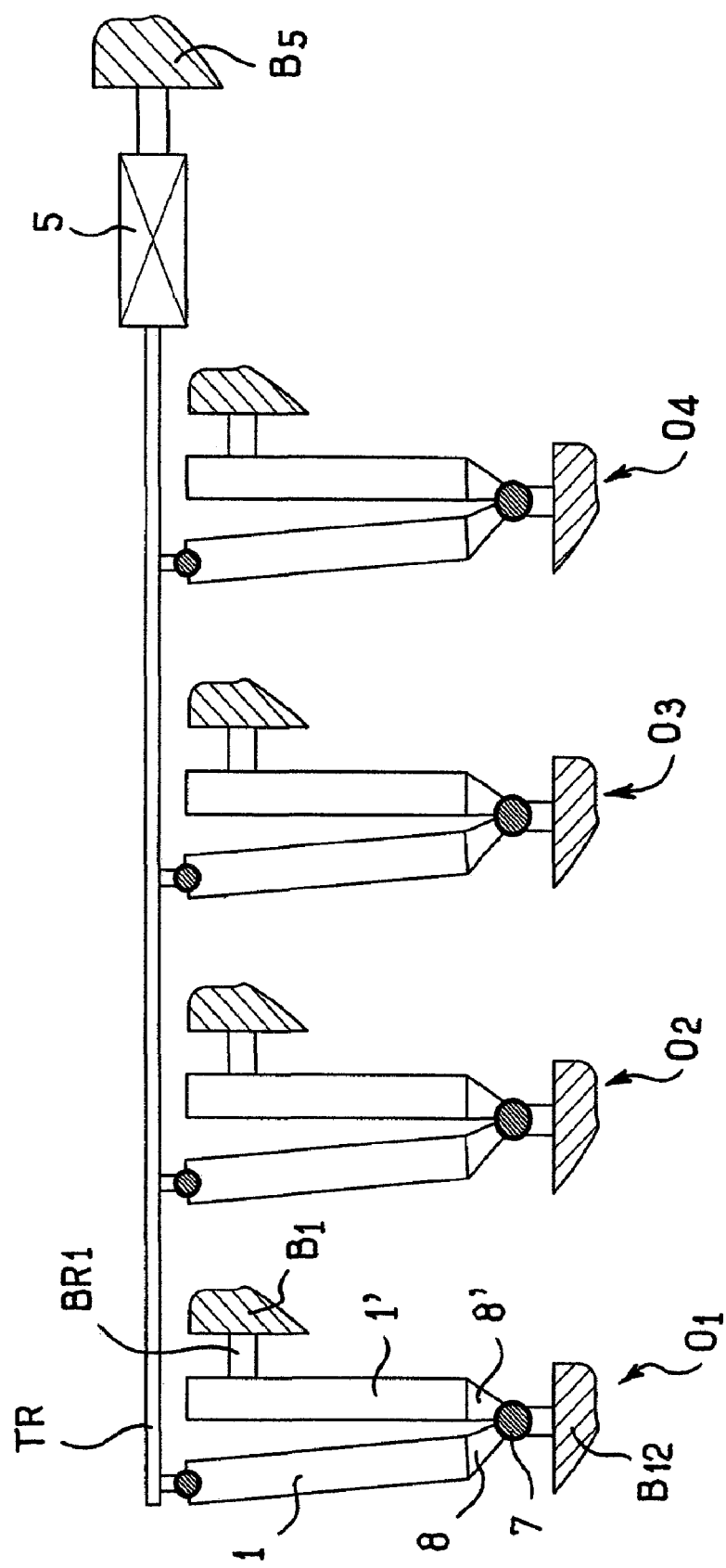
FIG. 10 is a diagrammatic elevation view showing a disuniting assembly having a plurality of tools of the invention.

In order to increase rates of throughput for industrial production, it is preferable to juxtapose a plurality of tools identical to the tool described above. Thus, as shown in FIG. 10, four tools $O_1$ to $O_4$ are mounted in parallel. With reference to the tool $O_1$, it can be seen that its plate 1' is connected to a portion of a fixed structure $B_{11}$ via a fixed arm $BR_1$. The pivot axis 7 between the plates 1 and 1' is mounted in a fixed position on another portion of the fixed structure $B_{12}$. The other three tools $O_2$ to $O_4$ are mounted identically. The plates 1 of the four tools $O_1$ to $O_4$ are actuated by a common rod TR, itself actuated by a common actuator 5, which also bears against another portion of the fixed structure $B_5$.

Naturally, in all of the embodiments above, the actuators of whatever kind are mounted via any suitable pivot, ball-and-socket joint, etc., enabling them to have the required degrees of freedom in flexing and pivoting.

At this point it should be observed that using hydraulic actuators provides disuniting energy levels that are entirely sufficient for the intended requirements, and in particular for use with bonding energies of the order of 1 J/m$^2$ or more.

In addition, the control and measurement of the pressures exerted and of the spacing required is much better than can be achieved with the techniques used in the past. In this respect, controlling the disuniting operation hydraulically with the ability to adjust finely the forces that are to be exerted makes it possible to vary disuniting conditions at will. It is also possible to make use of hydraulic pressure which raises in quasi-static manner, or in pulsed manner, which pulses can be isolated or repetitive, etc.

In this respect, when disuniting using conventional techniques, in a direction which is generally perpendicular to the substrate, variations are observed in the result depending on the way in which stress is applied. With the present invention, this latitude of utilization makes it possible additionally to study the dynamics of disuniting, in particular when fracturing a zone that has been weakened by using a SMART-CUT® method. It should also be observed that the tool of the present invention makes it possible to work at temperatures other than ambient temperature. In this respect, some kinds of bonding take place a temperatures of 150° C. and higher, and it will be understood that it is advantageous, for example for reasons of differential expansion, to be able to perform disuniting likewise at high or low temperatures. The person skilled in the art knows how to design the various parts constituting a tool as a function of the temperatures to which it is to be exposed.

The advantages of the present invention are now described.

The main advantage of the tool and of the associated technique is to be able to perform disuniting by applying stress that can possibly be very large, but without breaking nor even damaging the detached wafers. In this respect, by controlling flexing of the plates, it is possible to exert a large force close to one edge of the wafers to be disunited without inducing excessive flexing of said wafers, and on each occasion initiating disuniting in the weakest plane (contrary to techniques that make use of a blade).

As mentioned, the disuniting energy that is applied may be very large. It is limited practically only by the suction force applied through the diaphragms 102, 102'. This tool thus makes it possible to disunite so-called "dismountable" substrates where bonding energies are very high.

As also mentioned, by using hydraulic or equivalent actuators, the invention makes it possible to modulate energy as a function of time. In particular, during development stages prior to production, it is possible specifically to investigate responses to different applied pressures such as energy pulses (shock dynamics), or to variations of energy that on the contrary are very slow, or to repeated pulses suitable for giving rise to fatigue fractures.

Finally, and above all, by controlling the bending of the plates 1, 1' and thus of the wafers 2, 2' while they are being disunited, and by doing so independently of the traction that is exerted for disuniting purposes, it is possible to preserve said wafers. Thus, unlike techniques using a blade, the present case avoids plastic deformation or even breakage of the wafers while they are being disunited.

Another advantage provided by precise control of wafer bending, as compared with blade systems which cause each of the wafers to be deformed as a function of its own capacity for deformation (associated with its Young's modulus, its diameter, and its thickness), is that it is possible to preserve one of the two wafers (for example a wafer carrying a fragile layer or an active layer of a component) by keeping it plane, with bending being imposed on the other wafer, even if the other wafer is more rigid.

Finally, for research and development activity, the present invention is useful in several regards. Thus, contrary to techniques that make use of a blade, the present invention makes it possible to measure bonding energy by stopping propagation of the disuniting front at any time. In addition, the actuators can at all times deliver accurate and direct measurements of the applied stress and no mathematical computation is needed in addition.

Numerous variants can be applied to the invention. In particular, in a variant, the gripper plates 1, 1' can be secured to the wafers 2, 2' that are to be disunited by bonding using electrostatic forces, by bringing the set of wafers 2, 2' and the plates 1, 1' to appropriate potentials.

In particular, Coulomb or Johnson-Rahbeck electrostatic force plates and proposed in U.S. Pat. No. 6,351,367 or 6,215,643 can be used instead of the suction plates described above. Such plates are generally made of a dielectric material coating a metal electrode. A potential applied to the electrode, for example of the order of a few hundreds of volts, enables bonding forces to be generated that can be as great as about 500 grams per square centimeter ($g/cm^2$), which force is entirely suitable for use in the context of the present invention.

What is claimed is:

1. A method of disuniting two wafers, with at least one of the wafers being used in fabricating substrates for microelectronics, optoelectronics, or optics, the method comprising the following steps: temporarily affixing two gripper members to respective opposite faces of the wafers; and sufficiently displacing one of the gripper members relative to the other for inducing controlled flexing in at least one of the gripper members and for responsively exerting a force close to one edge of the wafers to assist in disuniting the wafers, wherein one or each gripper member comprises a body generally in the form of a plate having different degrees of elastic deformability in at least two locations.

2. The method of claim 1 which further comprises measuring the bonding energy between two wafers by measuring the force exerted during the displacement step or measuring the separation of the wafers while performing the disuniting operation.

3. The method of claim 2 wherein both the force exerted during the displacement step and the separation of the wafers is measured while performing the disuniting operation.

4. The method according to claim 1, wherein the temporary affixing step comprises contacting the gripper members with the wafer faces by applying a vacuum.

5. The method according to claim 1, wherein the temporary affixing step comprises providing the gripper members with the wafer faces by applying electrostatic forces.

6. The method according to claim 1, wherein the two gripper members are mounted to pivot relative to each other.

7. The method according to claim 1, wherein one or each gripper member comprises an electrode which has a different potential compared to that of a respective wafer face so as to provide temporary affixing by electrostatic forces.

8. The method according to claim 7, wherein each gripper member that includes an electrode further comprises dielectric material which surrounds the electrode.

* * * * *

UNITED STATES PATENT AND TRADEMARK OFFICE
CERTIFICATE OF CORRECTION

PATENT NO. : 7,740,735 B2
APPLICATION NO. : 11/567417
DATED : June 22, 2010
INVENTOR(S) : Kerdiles et al.

It is certified that error appears in the above-identified patent and that said Letters Patent is hereby corrected as shown below:

Title Page:
Item (30) Foreign Application Priority Data, change the priority application number from "02 16902" to -- 02 15902 --.

Signed and Sealed this

Third Day of August, 2010

David J. Kappos
*Director of the United States Patent and Trademark Office*